(12) United States Patent
Timoteo

(10) Patent No.: US 6,168,629 B1
(45) Date of Patent: Jan. 2, 2001

(54) FEMORAL COMPONENT FOR KNEE PROSTHESIS

(75) Inventor: Michel Timoteo, St Martin d'Uriage (FR)

(73) Assignee: Tornier S.A., Saint Ismier (FR)

( * ) Notice: Under 35 U.S.C. 154(b), the term of this patent shall be extended for 0 days.

(21) Appl. No.: 09/172,009

(22) Filed: Oct. 14, 1998

(30) Foreign Application Priority Data

Oct. 14, 1997 (FR) .................................................. 97 13072

(51) Int. Cl.$^7$ ....................................................... A61F 2/38
(52) U.S. Cl. ................................. 623/20.27; 623/20.14; 623/13.16
(58) Field of Search ................................. 623/20, 20.14, 623/20.2, 20.23, 20.27, 20.29, 20.31, 13.16; 3/1.91, 191

(56) References Cited

U.S. PATENT DOCUMENTS

| | | | |
|---|---|---|---|
| 3,990,117 | * 11/1976 | Pritchard et al. | ........................ 3/1.91 |
| 4,662,889 | * 5/1987 | Zichner et al. | ......................... 623/20 |
| 4,888,021 | * 12/1989 | Forte et al. | .............................. 623/20 |
| 5,116,375 | 5/1992 | Hofmann | ................................ 623/20 |
| 5,405,398 | * 4/1995 | Buford, III et al. | ................... 623/20 |
| 5,549,687 | 8/1996 | Coates et al. | ........................... 623/20 |

* cited by examiner

Primary Examiner—V. Millin
Assistant Examiner—Hieu Phan
(74) Attorney, Agent, or Firm—Greenblum & Bernstein, P.L.C.

(57) ABSTRACT

Femoral component for a knee prosthesis adapted to cooperate with an insert attached to a tibial plateau anchored at the upper end of a tibia. The femoral component is adapted to be anchored at a lower end of a femur, the femoral component including a first lateral condyle, a second lateral condyle, and an intercondylar space disposed between the first and second condyles for receiving a third removably fixed condyle. The third condyle is removable from the intercondyle space while the femoral component remains moveably engaged with the tibial plateau. The third condyle is adapted to provide posterior stabilization of the prosthesis during flexion between the tibia and the femur when the posterior cruciate ligament is no longer able to substantially perform its function.

24 Claims, 2 Drawing Sheets

FEMORAL COMPONENT FOR KNEE PROSTHESIS

BACKGROUND OF THE INVENTION

1. Field of the Invention

The invention relates to a femoral component for a knee prosthesis.

2. Description of Background and Relevant Information

The conventional femoral component of a knee prosthesis consists, of two lateral condyles, namely an external condyle and an internal condyle which define an intercondylar space. This lateral condyles are intended to cooperate with an insert attached to a tibial plateau, which is itself anchored at the upper end of the tibia.

This type of femoral component is typically used when a knee prosthesis is being fitted on a patient whose ligaments, and in particular the posterior cruciate ligament, are in a correct state, that is to say when they are able to maintain the femoral component on the insert/tibial plateau assembly, thereby preventing any drawer movement.

In case when the posterior cruciate ligament is no longer able to perform its function, the femoral component is replaced with a femoral component in which the intercondylar space is partly obturated by a third condyle, and thus permits posterior stabilization of the prosthesis during flexion of the tibia on the femur.

In view of these two types of cases, there is a need to provide a single femoral component which could be used either in the presence or absence of the posterior cruciate ligament.

One type of femoral component has been described in particular in the document FR-A-2 710 258, which proposes fitting, within the intercondylar space, a retractable support component which is able to receive a third condyle.

In practice, when it is not necessary to replace the posterior cruciate ligament, the surgeon implants the femoral component in a definitive manner, without fixing the third condyle thereto.

However, in the absence of the posterior cruciate ligament, the surgeon fits the third condyle into place before implanting the femoral component.

Unfortunately, once the prosthesis is fitted on a knee which still has its posterior cruciate ligament, this type of femoral component does not allow a third condyle to be fitted in the event of the ligament subsequently rupturing, without completely removing the femoral component from the femur, which causes considerable trauma.

SUMMARY OF THE INVENTION

The object of the invention is therefore to provide a femoral component for a knee prosthesis on which a third condyle can be fitted at any time, such as, before, during, and after the femoral component has been implanted. And such fitting can occur without having to remove the femoral component from the femur.

The invention therefore provides a femoral component for a knee prosthesis intended to cooperate with an insert attached to a tibial plateau which is anchored at the upper end of the tibia, the femoral component itself being anchored at the lower end of the femur and having two lateral condyles which cooperate with the insert and define an intercondylar space which is able to receive a third, removable condyle.

The femoral component provides each of the two lateral condyles with arrangements permitting the fitting or removal of a third condyle even after the anchoring of the femoral component on the femur.

In other words, the invention allows the third condyle to be fitted on a femoral component, even after it has been anchored definitively in the femur. This fitting, for example, will occur when it becomes necessary to remove the posterior cruciate ligament.

According to one embodiment of the invention, the arrangements consist of at least one through orifice formed on the lateral faces of each of the two lateral condyles, the orifices being intended to receive at least one device for securing the third condyle to the two lateral condyles.

Advantageously, there are two orifices and they are formed along a vertical axis.

To allow the third condyle to be fitted in the area of the two lateral condyles, the third condyle has complementary arrangements intended to cooperate with the arrangements on the lateral condyles.

In practice, the complementary arrangements consist of at least one through orifice formed on the lateral faces of the third condyle.

Advantageously, there are two orifices per face and they are aligned with the orifices provided on the lateral faces of the lateral condyles.

In order to obtain posterior stabilization of the knee prosthesis during flexion of the tibia on the femur, the third condyle has a semicylindrical shape with a thickness smaller than that of the intercondylar space, each of the lateral faces of the third condyle being equipped with a protuberance intended to make contact with the inner lateral faces of the lateral condyles, those protuberances having two lateral orifices which are intended to be positioned in alignment with the orifices of the lateral condyles.

To allow the third condyle to be fixed to the lateral condyles in a removable manner, the securing devices consists of at least one screw, one end of which has a thread intended to cooperate with a thread formed in an orifice of one of the two lateral condyles.

Thus, when fitting the third condyle, it suffices to position each of the orifices in line with the other, then to introduce the screw through the orifices, and finally to screw it in so as to fix the third condyle on the femoral component.

BRIEF DESCRIPTION OF THE DRAWINGS

The invention and the advantages which derive therefrom will be clearer from the illustrative embodiment which follows, with reference to the attached figures.

DETAILED DESCRIPTION OF THE INVENTION

The general reference (1) designates the femoral component of the invention. The component includes, in a known manner, two lateral condyles 2,3 which define an intercondylar space 4.

This femoral component is intended to be anchored at the lower end of the femur, and also cooperates with an insert attached to a tibial plateau which is anchored at the upper end of the tibia. The insert and the tibia have not been shown because they are not directly the subject of the invention.

Figure 1:
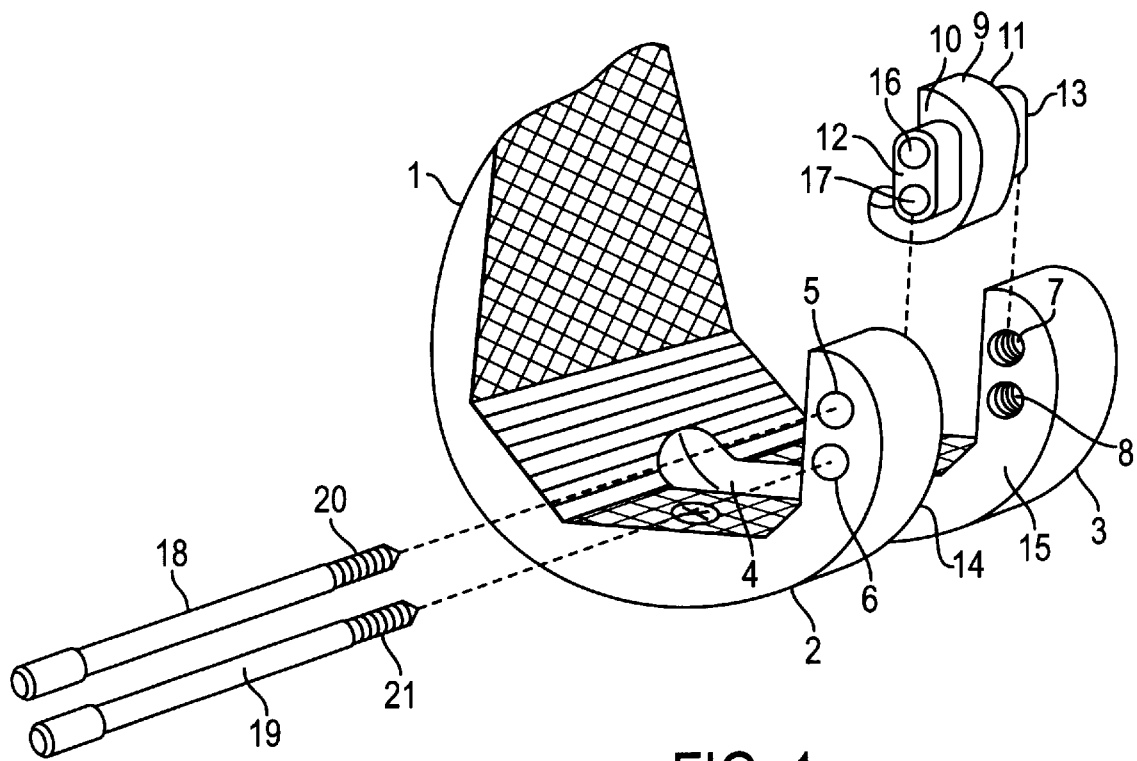
FIG. 1 is a perspective view of the femoral component of the invention.
Figure 5:
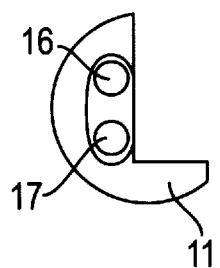
FIGS. 5 and 6 are diagrammatic representations, respectively from the side and from the front, of the third condyle according to the invention.
Figure 6:
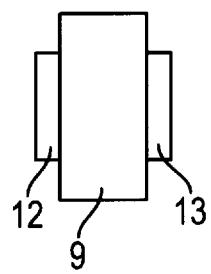

As FIG. 1 shows, each of the two lateral condyles 2,3 has, on their lateral face, two through orifices 5,6,7,8 formed along a vertical axis.

When the patient's posterior cruciate ligament is retained, the femoral component can be implanted as such at the lower end of the femur, without fitting the third condyle.

However when the posterior cruciate ligament is absent, it becomes necessary to implant a prosthesis with posterior stabilization.

To do this, third condyle 9 is fitted in the intercondylar space 4 at the free posterior ends of lateral condyles 2,3.

As has already been stated, third condyle 9 can be fitted even after femoral component has been implanted, without requiring the removal of femoral component 1.

According to a preferred embodiment of the invention, this third condyle 9 has a semicylindrical shape, with its width l being smaller than the width L of the intercondylar space.

Advantageously, third condyle 9 has, on each of its lateral faces 10,11, a protuberance 12,13 which is intended to come into contact with inner lateral faces 14,15 of lateral condyles 2,3. Each protuberance 12,13 additionally has two orifices 16,17 which are configured in such a way that once third condyle 9 is in place, they are in alignment with orifices 5 to 8 of lateral condyles 2,3.

When third condyle 9 is fitted to femur component, that is to say when all orifices are in alignment, a device for securing the third condyle 9 to the lateral condyles 2,3 is introduced through these aligned orifices.

In practice, this securing device is in the form of one or more screws 18,19, of which one end 20 is threaded and cooperates with a corresponding thread formed in the orifices of one of the two lateral condyles.

Thus, when third condyle 9 is to be fitted, it suffices to introduce screws 18,19 into the respective corresponding orifices 5,16 and 6,17 and then to lock screws 18,19 in the threaded orifice 7,8.

Figure 2:
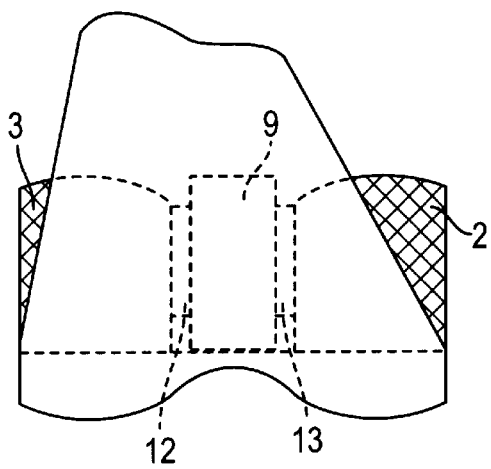
FIG. 2 is a view, in the anteroposterior direction, of the femoral component according to FIG. 1.

FIG. 2 shows femoral component 1 of the invention with third condyle 9 fitted thereto.

Figure 3:
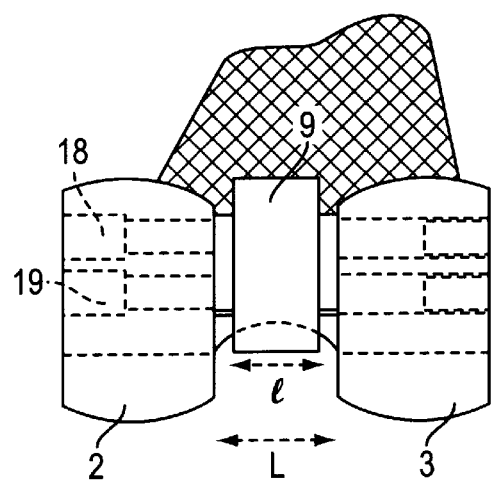
FIG. 3 is a view in the posteroanterior direction according to FIG. 1.
Figure 4:
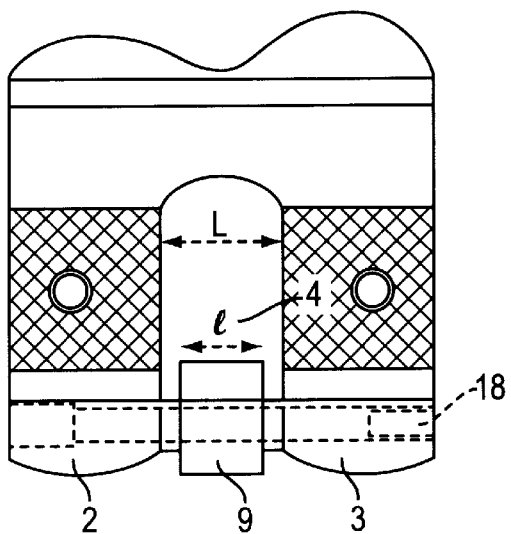
FIG. 4 is a plan view of the femoral component according to FIG. 1.

FIG. 3 shows the passage of the screws 18 and 19 in orifices 5,7,16 and 6,8,17 respectively.

As has already been stated, when the patient's knee is equipped with the posterior cruciate ligament, the surgeon implants the femoral component of the invention without third condyle 9.

If, subsequently, the posterior cruciate ligament ruptures or no longer performs its function, it is then possible for the surgeon to fit the third condyle 9 on the implanted prosthesis without having to remove the latter from the femoral bone. As a result, is possible to avoid any trauma to the bone.

The invention, as it has been described, thus affords a great number of advantages and in particular makes it possible to convert a knee prosthesis without posterior stabilization into a prosthesis with posterior stabilization by virtue of the peroperative or postoperative addition of a third condyle, and this without the femoral component having to be removed from the femur.

What is claimed is:

1. A femoral component for a knee prosthesis adapted to cooperate with an insert attached to a tibial plateau anchored at the upper end of a tibia, the femoral component adapted to be anchored at a lower end of a femur, the femoral component comprising:
   a first lateral condyle;
   a second lateral condyle; and
   an intercondylar space disposed between the first and second condyles for receiving a third removably fixed condyle;
   wherein the third condyle is configured to be selectively removed from the intercondyle space while the femoral component remains moveably engaged with the tibial plateau, the third condyle being configured to provide posterior stabilization of the prosthesis during flexion between the tibia and the femur when the posterior cruciate ligament is no longer able to substantially perform its function.

2. The femoral component of claim 1, wherein the first condyle comprises a lateral face having at least one opening and the second condyle comprises a lateral face having at least one opening, the openings being substantially aligned with one another and adapted to receive a device for securing the third condyle within the intercondylar space.

3. The femoral component of claim 2, wherein the third condyle comprises at least one through opening for receiving the device.

4. The femoral component of claim 3, wherein the device comprises a screw having threads which engage one of the first and second lateral condyles.

5. The femoral component of claim 2, further comprising at least two openings on the lateral face of each of the first and second condyles.

6. The femoral component of claim 5, wherein the third condyle comprises at least two through openings for receiving the device.

7. The femoral component of claim 6, wherein the device comprises a screw having threads which engage one of the first and second lateral condyles.

8. The femoral component of claim 1, wherein the third condyle comprises first and second lateral faces which are substantially parallel to one another and a semi-cylindrical surface which is substantially perpendicular to one of the first and second lateral faces.

9. The femoral component of claim 8, wherein the third condyle further comprises at least one protuberance disposed on each of the first and second lateral faces.

10. The femoral component of claim 9, wherein the first condyle comprises a lateral face having at least one opening, the second condyle comprises a lateral face having at least one opening, and the third condyle comprises at least one through opening which extends from the first lateral face to the second lateral face, the openings being substantially aligned with one another and adapted to receive a device for securing the third condyle within the intercondylar space.

11. A femoral component for a knee prosthesis adapted to cooperate with an insert attached to a tibial plateau anchored at the upper end of a tibia, the femoral component adapted to be anchored at a lower end of a femur, the femoral component comprising:
   a first lateral condyle;
   a second lateral condyle;
   an intercondylar space disposed between the first and second condyles; and
   a third condyle substantially disposed within the intercondylar space and removably fixed to at least one of the first and second condyles;
   wherein the third condyle is configured to be selectively removed from the femoral component when the femoral component moveably engages the tibial plateau.

12. The femoral component of claim 11, wherein the first condyle comprises a lateral face having at least one opening and the second condyle comprises a lateral face having at least one opening, the openings being substantially aligned with one another and adapted to receive at least one securing device.

13. The femoral component of claim 12, wherein the third condyle comprises at least one through opening for receiving the at least one securing device.

14. The femoral component of claim 13, wherein the at least one securing device comprises a screw having threads which engage one of the first and second lateral condyles.

15. The femoral component of claim 13, further comprising at least two openings on the lateral face of each of the first and second condyles, at least two through openings on the third condyle, and at least two securing devices for connecting the first, second, and third condyles via the through openings.

16. The femoral component of claim 15, wherein each of the at least two securing devices comprises a screw having threads which engage one of the first and second lateral condyles.

17. The femoral component of claim 11, wherein the third condyle further comprises a first and a second lateral face, each of the first and second lateral faces comprising a protuberance.

18. A femoral component for a knee prosthesis adapted to cooperate with a tibial component which is anchored at the upper end of a tibia, the femoral component adapted to be anchored at a lower end of a femur and comprising:

a first lateral condyle comprising a femur engaging surface and a curved surface for moveably engaging the tibial component;

a second lateral condyle comprising a femur engaging surface and a curved surface for moveably engaging the tibial component;

an intercondylar space disposed between the first and second condyles; and a removable third condyle at least partially disposed within the intercondylar space;

wherein the third condyle comprises a curved surface for moveably engaging the tibial component and a femur facing surface, the femur facing surface being disposed adjacent the femur when the third condyle is secured to the femoral component and wherein the third condyle is configured to be selectively removed from the intercondyle space while the femoral component remains moveably engaged with the tibial plateau.

19. The femoral component of claim 18, wherein the first condyle comprises a lateral face having at least one opening and the second condyle comprises a lateral face having at least one opening, the openings being substantially aligned with one another and adapted to receive at least one securing device.

20. The femoral component of claim 19, wherein the third condyle comprises at least one through opening for receiving the at least one securing device.

21. The femoral component of claim 20, wherein the at least one securing device comprises a screw having threads which engage one of the first and second lateral condyles.

22. The femoral component of claim 20, further comprising at least two openings on the lateral face of each of the first and second condyles, at least two through openings on the third condyle, and at least two securing devices for connecting the first, second, and third condyles via the through openings.

23. The femoral component of claim 22, wherein each of the at least two securing devices comprises a screw having threads which engage one of the first and second lateral condyles.

24. The femoral component of claim 18, wherein the third condyle further comprises a first and a second lateral face, each of the first and second lateral faces comprising a protuberance.

* * * * *